US006997044B1

(12) United States Patent
Maciejewski

(10) Patent No.: US 6,997,044 B1
(45) Date of Patent: Feb. 14, 2006

(54) TEST SYSTEM FOR A FLEXIBLE TUBE

(75) Inventor: Wendell C. Maciejewski, Wakefield, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/947,790

(22) Filed: Sep. 20, 2004

(51) Int. Cl.
*G01M 3/04* (2006.01)
(52) U.S. Cl. ......................................... 73/49.5; 73/49.8
(58) Field of Classification Search ................. 73/49.5, 73/49.8
See application file for complete search history.

(56) References Cited

U.S. PATENT DOCUMENTS

| | | | |
|---|---|---|---|
| 590,094 A | | 8/1897 | Duncan |
| 2,074,140 A | * | 3/1937 | Bates ........................... 223/61 |
| 2,453,056 A | | 11/1948 | Zack |
| 3,490,438 A | | 1/1970 | Lavender et al. |
| 3,495,443 A | * | 2/1970 | Switzer et al. ............ 73/40.5 R |
| 3,540,451 A | | 11/1970 | Zeman |
| 3,616,685 A | * | 11/1971 | Strom ........................... 73/84 |
| 3,851,899 A | | 12/1974 | Franz |
| 3,884,070 A | * | 5/1975 | Windle ........................ 73/49.8 |
| 3,991,604 A | * | 11/1976 | Hayes et al. .................... 73/37 |
| 4,122,858 A | | 10/1978 | Schiff |
| 4,192,177 A | * | 3/1980 | Crickard et al. .............. 73/49.5 |
| 4,354,379 A | * | 10/1982 | Miner ............................ 73/37 |
| 4,413,501 A | * | 11/1983 | Schrock ....................... 73/49.6 |
| 4,430,887 A | * | 2/1984 | Roberts et al. .............. 73/49.5 |
| 4,486,035 A | | 12/1984 | Storke |
| 4,519,636 A | | 5/1985 | Tomlin et al. |
| 4,570,485 A | * | 2/1986 | Lee, Jr. ........................ 73/49.5 |
| 4,838,075 A | * | 6/1989 | Friedrich et al. ............ 73/49.8 |
| 4,852,393 A | * | 8/1989 | Pate et al. ................... 73/49.5 |
| 4,858,464 A | * | 8/1989 | Miller et al. ................. 73/49.5 |
| 5,220,824 A | * | 6/1993 | Shelleman et al. .......... 73/49.5 |
| 5,255,558 A | * | 10/1993 | Hamilton ....................... 73/40 |
| 5,442,952 A | * | 8/1995 | Morris et al. ................ 73/40.7 |
| 5,587,521 A | * | 12/1996 | Lanasa ......................... 73/49.1 |

* cited by examiner

*Primary Examiner*—Hezron Williams
*Assistant Examiner*—John Fitzgerald
(74) *Attorney, Agent, or Firm*—James M. Kasischke; Michael P. Stanley; Jean-Paul A. Nasser

(57) ABSTRACT

A system is provided for testing a flexible tube. First and second hollow mandrels are inserted into opposing ends of the tube. Each mandrel has a conically tapered portion at one end thereof and a cylindrical portion extending from the conically tapered portion. The cylindrical portion has a plurality of annular indentations formed thereabout. Each of a plurality of clamps encircle the tube in line with one annular indentation to sealably engage the tube. A fluid delivery system is coupled between the cylindrical portions of the mandrels to deliver a flow of fluid through the tube via the mandrels. A measured strain producing load, continuous or cyclical, is applied by an apparatus which controllably moves the first mandrel relative to the second mandrel such that a cross-sectional shape of the tube between the mandrels is altered.

16 Claims, 2 Drawing Sheets

TEST SYSTEM FOR A FLEXIBLE TUBE

STATEMENT OF GOVERNMENT INTEREST

Figure 1:
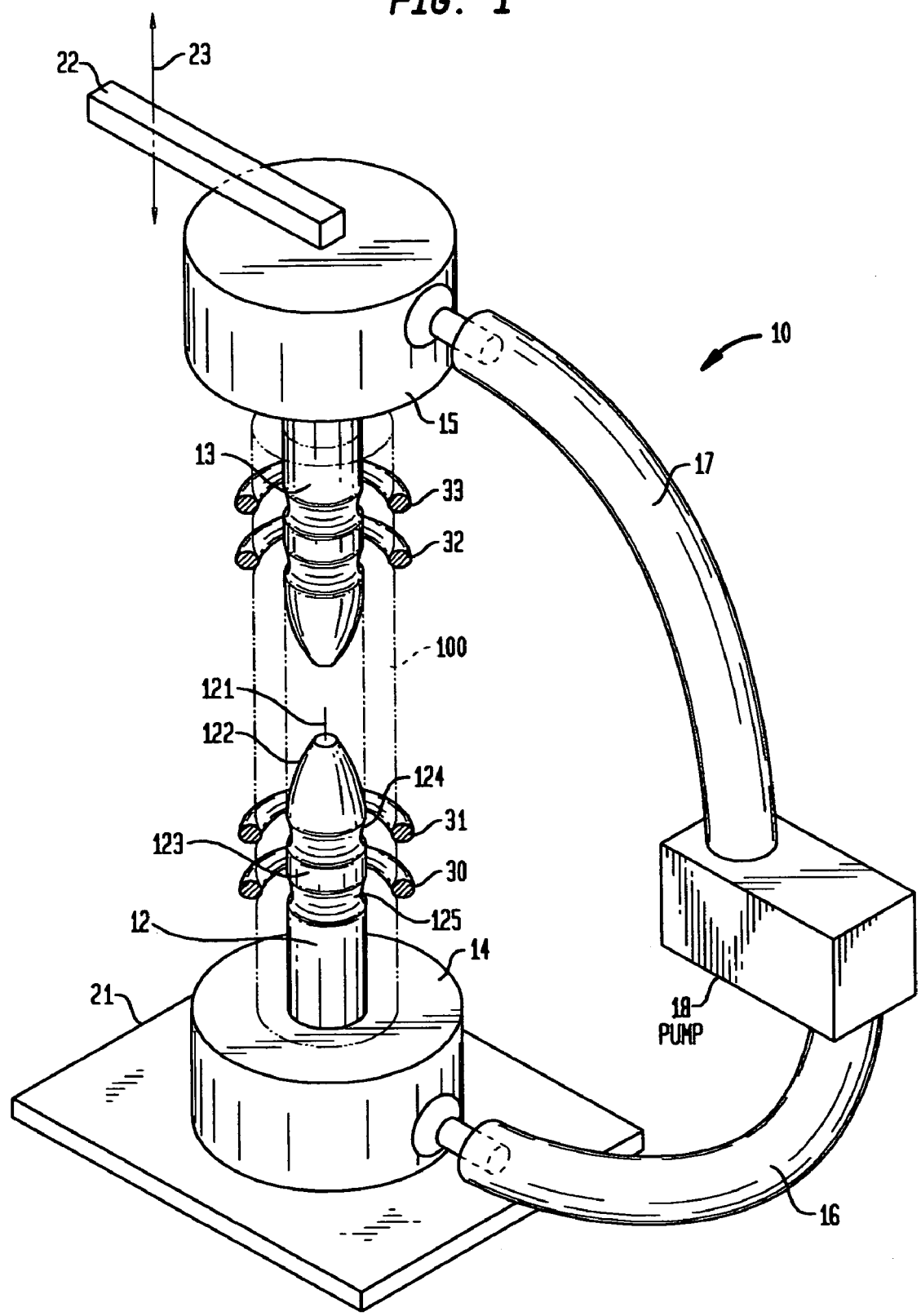

The invention described herein may be manufactured and used by or for the Government of the United States of America for Governmental purposes without the payment of any royalties thereon or therefor.

BACKGROUND OF THE INVENTION (1) Field of the Invention

The present invention relates generally to testing of flexible tubes, and more particularly to a system for testing a flexible tube, e.g., biomedical tubes, that minimizes unwanted stress on the tube while simulating an actual use environment.

(2) Description of the Prior Art

In many applications involving the use of flexible tubing, it is desirable to determine the tube's mechanical properties and to know how the tubing will react under load conditions. Accordingly, sample lengths of the purposed tubing must be tested in either actual use or in a test environment. In cases where tube performance is critical (e.g., shock testing, environmental and hazardous material testing, biomedical tube applications to include artificial arteries and other biofluid ducts), testing in an actual use environment is not an option. Thus, many types of flexible tubing must rely on lab testing.

Currently, it is difficult to grip materials such as thin-walled tubing in a manner that does not distort the cylindrical shape. Conventional lab testing techniques generally pinch the ends of the tube such that the resulting shape is no longer cylindrical. The shape distortion causes stress concentrations to develop in the gripping area that can lead to premature failure. However, the shape change in the gripping area can also negatively affect areas along the test section of the tube. In addition, there are no practical test means of holding flexible tubes while applying an internal pressure to them for the purposes of testing the tube's fluid transport performance while under a loaded condition.

SUMMARY OF THE INVENTION

Accordingly, it is an object of the present invention to provide a system for testing a flexible tube.

Another object of the present invention is to provide a system for testing a flexible tube that minimizes unwanted tube distortion.

Still another object of the present invention is to provide a system for testing the fluid handling performance of the flexible tube as the flexible tube experiences load conditions.

Other objects and advantages of the present invention will become more obvious hereinafter in the specification and drawings.

In accordance with the present invention, a system for testing a flexible tube includes first and second hollow mandrels inserted into opposing ends of the tube undergoing test. Each mandrel has a conically tapered portion at one end thereof within the tube and a cylindrical portion extending from the conically tapered portion. The cylindrical portion has an outside surface that undulates such that a plurality of annular indentations are formed thereabout within the tube. Each of a plurality of clamps encircle the tube in line with one annular indentation to circumferentially compress the tube into the respective annular indentation. In this way, the outside surface of each mandrel is sealably engaged with the tube. A fluid delivery system is coupled between the cylindrical portions of the mandrels for pumping a fluid through the tube via the mandrels. A loading apparatus controllably moves the first mandrel relative to the second mandrel such that a cross-sectional shape of the tube between the mandrels is altered.

BRIEF DESCRIPTION OF THE DRAWING(S)

Figure 2:
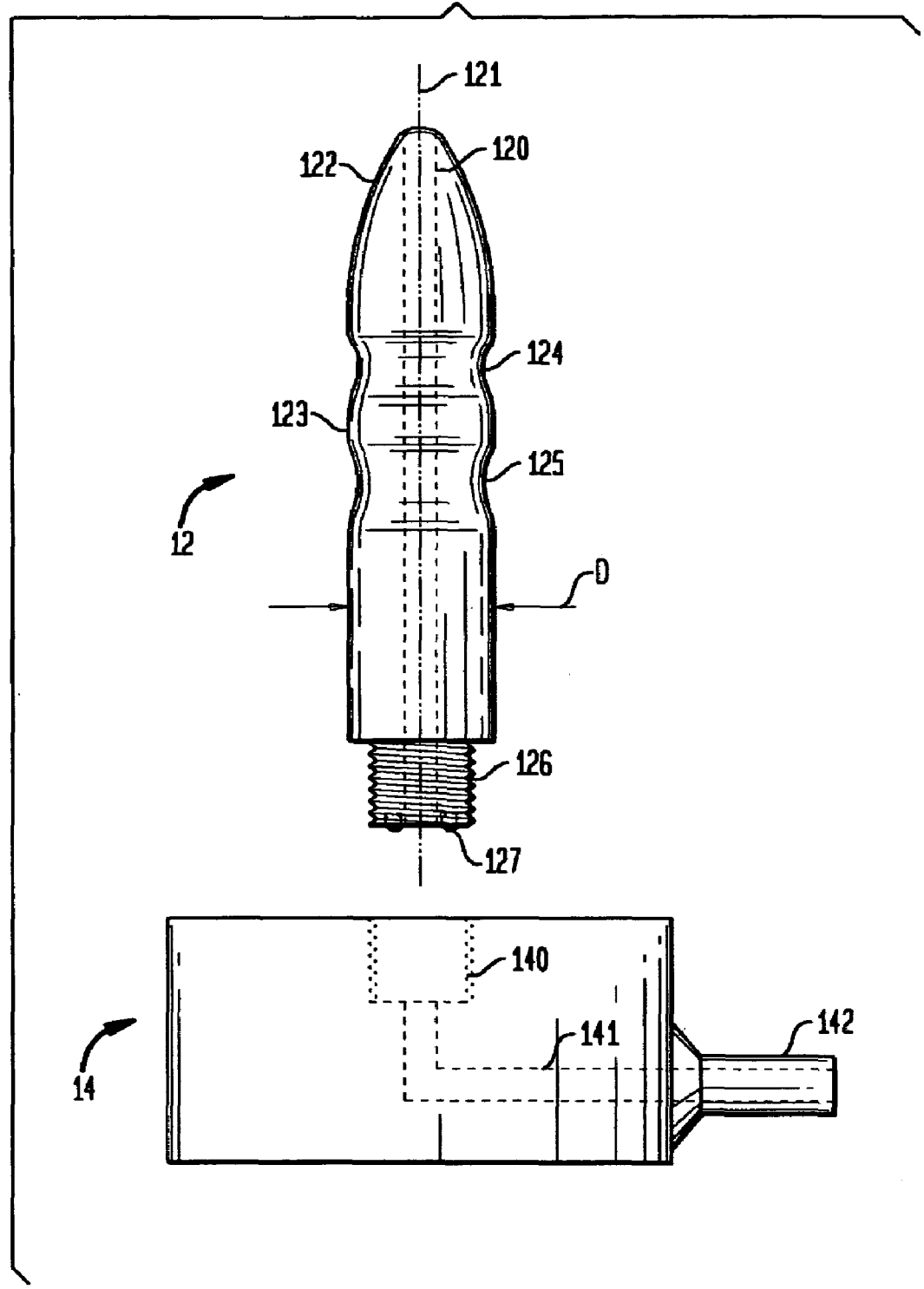

Other objects, features and advantages of the present invention will become apparent upon reference to the following description of the preferred embodiments and to the drawings, wherein:

FIG. 1 is, in part, a perspective view and, in part, a schematic view of the system for testing a flexible tube in accordance with the present invention; and FIG. 2 is an exploded side view of the hollow mandrel and base used in a preferred embodiment of the invention.

DESCRIPTION OF THE PREFERRED EMBODIMENT(S)

Referring now to the drawings, and more particularly to FIG. 1, a system is shown for testing a flexible tube 100 (shown in phantom) and is referenced generally by numeral 10. System 10 includes mandrels 12, 13 supported by respective bases 14, 15. Coupled to each base 14, 15 is a respective hose lead 16, 17 connected to pump 18 which can be a constant-pressure or cyclic-pressure pump for pumping fluid through tube 100 as will be explained further below.

System 10 can also include an apparatus or mechanism for causing tube 100 to experience strain causing load conditions, e.g., tension, compression, etc. For example, if tube 100 were to be used as an artificial artery or as part of any dynamic solid, liquid or gaseous transport system, a test machine capable of applying tensile or compressive cyclic loads could be coupled to bases 14, 15. In general, the test machine would include a stationary platen 21 to which base 14 is attached and a moveable platen 22 to which base 15 is attached. The movement of platen 22 relative to platen 21, indicated by arrow 23, delivers the desired-load, e.g., constant tension, constant compression or cyclical tension and compression.

Referring additionally now to FIG. 2, a preferred embodiment construction of mandrel 12 and base 14 will be explained in greater detail. It is to be understood that similar construction details exist for mandrel 13 and base 15. Mandrel 12 is hollow with a bore or passage 120 extending therethrough along the central longitudinal axis 121. One end 122 is smoothly tapered while the main body portion 123 extending from (tapered) end 122 is generally cylindrical. However, the outside surface of main body portion 123 undulates along the length thereof to form at least one and, preferably, a plurality (two are shown) of annular indentations or grooves 124, 125 about the perimeter of main body portion 123. Typically, the annular indentations lie in planes that are perpendicular to central longitudinal axis 121. The largest outside diameter D of the combination of tapered end 122 and main body portion 123 is equal to or slightly less than the inside diameter of tube 100 when tube 100 is in its relaxed state. In this way, mandrel 12 does not stress or distort the shape of tube 100 as mandrel 12 is inserted in an end thereof.

To couple mandrel 12 to base 14, mandrel 12 is threaded at end 126 as shown. A mating threaded connection 140 is provided at base 14. To form a good fluid seal between mandrel 12 and base 14, an O-ring 127 is provided at end 126 (or alternatively can be provided within threaded connection 130). A passage 141 through base 14 couples a mounting conduit 142 to the open area of connection 140 and, ultimately, to passage 120 of mandrel 12. Hose lead 16 is coupled to mounting conduit 142.

Referring again to FIG. 1, each mandrel 12, 13 is inserted partially or fully into tube 100 such that the annular indentations thereof, e.g., annular indentations 124, 125, are within tube 100. The tapered ends of the mandrels, e.g., end 122, facilitates the initial insertion of each mandrel into tube 100 while the diameter of each main body portion permits them to slide easily into position within tube 100. The smooth taper of end 122 also allows tube 100 to be deformed (i.e., stretched) without damage to the inner walls of tube 100. In other words, when the cross-section of tube 100 is reduced about end 122, the inner surface of tube 100 does not contact any rough or sharp edges of mandrel 12.

Once in position within tube 100, each of mandrels 12, 13 is fixed relative to tube 100 by means of at least one and, preferably, a plurality of clamps that cooperate with tube 100 and the annular indentation(s) 124, 125 on each mandrel 12, 13. In the example of FIG. 1, clamps 30 and 31 are provided for mandrel 12 and clamps 32 and 33 are provided for mandrel 13. Each of clamps 30, 31, 32, 33 is a "circular" clamp capable of applying a generally even circumferential pressure about tube 100 at a respective annular indentation of one of the mandrels. In this way, tube 100 is positively engaged with the mandrels to provide a good mechanical coupling and a good fluid seal. The mechanical coupling allows tube 100 to have loads applied thereto while the fluid seal allows tube 100 to be tested simultaneously for fluid handling performance. In addition, clamps 30, 31, 32 and 33 can be selected to be the same type of clamp that would be used in an actual use environment. For example, if tube 100 is an artificial artery, each of clamps 30, 31, 32 and 33 could be a suture clamp. In this way, testing is extended to include the support components related to tube 100 as they would be used in the actual application.

In operation, once each mandrel is secured with its respective clamps to tube 100, pump 18 and moveable platen 22 can be operated in a desired fashion. For example, pump 18 could be operated cyclically to simulate blood being pumped through tube 100 (via the hose leads, bases and mandrels), while the combination of stationary platen 21 and moveable platen 22 applied various loads to tube 100 via mandrels 12, 13.

The advantages of the present invention are numerous. The design of each mandrel minimizes any unwanted stress or distortion of the tube sample during test set-up and test runs. The combination of circular clamps cooperating with the annular indentations on each mandrel provides both mechanical and fluid seal coupling necessary to test the tube dynamically.

With the present invention installed in a suitable test machine such as in Instron Universal Test Machine Model 4206 manufactured by Instron Corporation, Canton, Mass., loads and strains can be monitored as a function of flow rates and pressures. It provides for a simple means of evaluating the mechanical behavior of tube materials without having to destroy the actual tube geometry. Extensometers and strain gages can be used to outfit the tube samples such that strains in all directions can be monitored. The invention can also be designed small enough to fit inside conventional temperature or pressure chambers which can provide other degrees of accuracy in terms of simulating the actual use environment.

It will be understood that many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. A system for testing a flexible tube, comprising:
   first and second hollow mandrels adapted to be inserted into opposed marginal end portions of a flexible tube, each of said first and second hollow mandrels having a conically tapered portion at one end thereof within the flexible tube, each of said first and second hollow mandrels having a cylindrical portion extending from said conically tapered portion, said cylindrical portion having an outside surface that undulates to form at least one annular indentation about each said cylindrical portion within the flexible tube;
   at least one clamp encircling the flexible tube and aligned with the at least one annular indentations for circumferentially compressing a portion of the flexible tube into said at least one annular indentation to thereby cause sealing engagement between said first and second hollow mandrels and the flexible tube; and,
   first means coupled between said cylindrical portions of said first and second hollow mandrels for generating a flow of fluid through the flexible tube.

2. A system as in claim 1 further comprising a plurality of annular indentations formed around said first and second hollow cylindrical portions and a respective plurality of clamps aligned with said plurality of annular indentations.

3. A system as in claim 1 wherein said at least one annular indentations associated with said first hollow mandrel is perpendicular to a longitudinal axis of said first hollow mandrel, and wherein said at least one annular indentations associated with said second hollow mandrel is perpendicular to a longitudinal axis of said second hollow mandrel.

4. A system as in claim 1 wherein the flexible tube is a biomedical tube and said at least one clamp is a suture clamp.

5. A system as in claim 1 wherein central longitudinal axes of said first and second hollow mandrels are aligned with one another.

6. A system as in claim 1 wherein said first means comprises a constant pressure pump for supplying said flow of fluid at a constant pressure.

7. A system as in claim 1 wherein said first means comprises a cyclic pump for supplying said flow of fluid at a cyclical pressure.

8. A system as in claim 1 wherein each of said first and second mandrels has an outside diameter which does not exceed the inside diameter of the flexible tube.

9. A system as in claim 1 further comprising second means for controllably moving said first hollow mandrel relative to said second hollow mandrel to thereby place a straining load upon the flexible tube and in turn thereby altering a cross-sectional shape of the flexible tube between said first and second hollow mandrels.

10. A system for testing a flexible tube, comprising:
    first and second hollow mandrels, each of said first and second hollow mandrels defining a flow passage therethrough, each of said first and second hollow mandrels having an outside diameter which does not exceed the diameter of a bore of the flexible tube, said first and second hollow mandrels partially adapted to be inserted into opposed marginal end portions of the flexible tube, each of said first and second hollow mandrels having a conically tapered portion at one end thereof within the flexible tube, each of said first and second hollow mandrels having a cylindrical portion extending from said conically tapered portion, said cylindrical portion having an outside surface that undulates to form a plurality of annular indentations about each said cylindrical portion within the flexible tube;

each of a like plurality of clamps encircling the flexible tube and aligned with one of said plurality of annular indentations for circumferentially compressing a portion of the flexible tube into said one of said plurality of annular indentations to thereby cause sealing engagement between said first and second hollow mandrels and the flexible tube;

a first base coupled to a free end of said cylindrical portion of said first hollow mandrel, said first base defining a passage that communicates with said flow passage of said first hollow mandrel;

a second base coupled to a free end of said cylindrical portion of said second hollow mandrel, said second base defining a passage that communicates with said flow passage of said second hollow mandrel;

a loading apparatus coupled to said first base and said second base for delivering a load thereto, wherein said load is transferred to the flexible tube via said first and second hollow mandrels to thereby cause a straining load in the flexible tube; and a fluid delivery system coupled between said passage of said first base and said passage of said second base for generating a flow of fluid through the flexible tube via said first and second hollow mandrels.

11. A system as in claim 10 wherein each of said plurality of annular indentations associated with said first hollow mandrel is perpendicular to a longitudinal axis of said first hollow mandrel, and wherein each of said plurality of annular indentations associated with said second hollow mandrel is perpendicular to a longitudinal axis of said second hollow mandrel.

12. A system as in claim 10 wherein the flexible tube is a biomedical tube and each of said plurality of clamps is a suture clamp.

13. A system as in claim 10 wherein said fluid delivery system includes a constant pressure pump for supplying said flow of fluid at a constant pressure.

14. A system as in claim 10 wherein said fluid delivery system includes a cyclic pump for supplying said flow of fluid at a cyclical pressure.

15. A system as in claim 10 wherein central longitudinal axes of said first and second hollow mandrels are aligned with one another.

16. A system as in claim 15 wherein said straining load is an oscillating load applied along said central longitudinal axes.

* * * * *